US012121368B2

(12) United States Patent
Dang et al.

(10) Patent No.: US 12,121,368 B2
(45) Date of Patent: Oct. 22, 2024

(54) EMBEDDED ORAL SENSOR PLATFORM

(71) Applicant: International Business Machines Corporation, Armonk, NY (US)

(72) Inventors: Bing Dang, Chappaqua, NY (US); Rajeev Narayanan, Briarcliff Manor, NY (US); Jeffrey L. Rogers, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 710 days.

(21) Appl. No.: 17/095,101

(22) Filed: Nov. 11, 2020

(65) Prior Publication Data

US 2022/0142571 A1 May 12, 2022

(51) Int. Cl.
*A61B 5/00* (2006.01)
*A61B 5/01* (2006.01)
(Continued)

(52) U.S. Cl.
CPC .............. *A61B 5/682* (2013.01); *A61B 5/002* (2013.01); *A61B 5/01* (2013.01); *A61B 5/0534* (2013.01);
(Continued)

(58) Field of Classification Search
CPC ........... A61B 5/682; A61B 5/002; A61B 5/01; A61B 5/0534; A61B 5/0537;
(Continued)

(56) References Cited

U.S. PATENT DOCUMENTS 6,089,864 A 7/2000 Buckner
10,251,729 B1 * 4/2019 Raslambekov .......... A61C 7/36
(Continued)

FOREIGN PATENT DOCUMENTS

CN 104921833 A 9/2015
CN 105792736 A 7/2016
(Continued)

OTHER PUBLICATIONS

"Patent Cooperation Treaty PCT Notification of Transmittal of the International Search Report and the Written Opinion of the International Searching Authority, or the Declaration", Applicant's file reference PF210862PCT, International application No. PCT/CN2021/127949, International filing date Nov. 1, 2021 (Nov. 1, 2021), Date of mailing Jan. 26, 2022 (Jan. 26, 2022), 11 pages.
(Continued)

*Primary Examiner* — May A Abouelela
(74) *Attorney, Agent, or Firm* — Amin, Turocy & Watson, LLP (57) ABSTRACT

Embodiments of the present invention provide an oral device. According to one embodiment of the present invention, a mouthpiece suitable to detachably engage teeth of an upper jaw is provided. The mouthpiece comprises an adhesive layer configured to attach a hermetically sealed chamber to the mouthpiece. The hermitically sealed chamber fits within a concave space created by the mouthpiece. The hermitically sealed chamber comprises two layers and embedded between those two layers are a pressure sensor, a microphone, an optical sensor, a temperature sensor, a communications module, a storage enclosure, and a biosensor. Each of the pressure sensor, the microphone, the optical sensor, the temperature sensor, the communications module, the storage enclosure, and the biosensor are operably connected within the hermetically sealed chamber.

11 Claims, 8 Drawing Sheets

(51) Int. Cl.

| | |
|---|---|
| *A61B 5/0534* | (2021.01) |
| *A61B 5/0537* | (2021.01) |
| *A61B 5/0538* | (2021.01) |
| *A61B 5/08* | (2006.01) |
| *A61B 5/145* | (2006.01) |
| *A61B 5/1473* | (2006.01) |
| *A61B 5/22* | (2006.01) |

(52) U.S. Cl.
CPC .......... *A61B 5/0537* (2013.01); *A61B 5/0538* (2013.01); *A61B 5/0816* (2013.01); *A61B 5/14539* (2013.01); *A61B 5/14542* (2013.01); *A61B 5/1473* (2013.01); *A61B 5/228* (2013.01); *A61B 5/4277* (2013.01); *A61B 5/4542* (2013.01); *A61B 5/4818* (2013.01); *A61B 5/4884* (2013.01); *A61B 2562/0247* (2013.01); *A61B 2562/0261* (2013.01); *A61B 2562/028* (2013.01); *A61B 2562/16* (2013.01)

(58) Field of Classification Search
CPC . A61B 5/0538; A61B 5/0816; A61B 5/14539; A61B 5/14542; A61B 5/1473; A61B 5/228; A61B 5/4277; A61B 5/4542; A61B 5/4818; A61B 5/4884; A61B 2562/0247; A61B 2562/0261; A61B 2562/028; A61B 2562/16; A61B 5/6835; A61B 5/4557; A61F 2005/563; A61F 5/566
See application file for complete search history.

(56) References Cited

U.S. PATENT DOCUMENTS

| | | | |
|---|---|---|---|
| 10,470,847 B2* | 11/2019 | Shanjani | H04B 5/0056 |
| 10,517,525 B2* | 12/2019 | Yoon | A61B 5/681 |
| 11,064,913 B2* | 7/2021 | Gonzales | A61B 5/11 |
| 11,109,808 B2* | 9/2021 | Yoon | A61B 5/02416 |
| 2005/0113654 A1 | 5/2005 | Weber | |
| 2009/0221884 A1 | 9/2009 | Ryan | |
| 2010/0311003 A1* | 12/2010 | Kozlov | A61F 5/566 |
| | | | 128/848 |
| 2011/0184319 A1 | 7/2011 | Mack | |
| 2012/0172677 A1 | 7/2012 | Logan | |
| 2013/0000652 A1* | 1/2013 | Fisher | A61F 5/566 |
| | | | 128/862 |
| 2013/0211270 A1 | 8/2013 | Bryan | |
| 2013/0253286 A1 | 9/2013 | Fridman | |
| 2014/0190489 A1* | 7/2014 | Chen | A61F 5/566 |
| | | | 128/848 |
| 2014/0329192 A1 | 11/2014 | Kaskoun | |
| 2015/0164682 A1* | 6/2015 | Remmers | A61B 5/4836 |
| | | | 600/529 |
| 2016/0157962 A1* | 6/2016 | Kim | B29C 65/48 |
| | | | 156/242 |
| 2016/0230007 A1* | 8/2016 | Johnson | C08L 91/06 |
| 2016/0242692 A1* | 8/2016 | McAuliffe | A61B 5/228 |
| 2017/0056131 A1 | 3/2017 | Alauddin | |
| 2017/0151400 A1* | 6/2017 | Vaska | A61M 16/0488 |
| 2017/0265978 A1* | 9/2017 | Borotto | A61C 19/05 |
| 2017/0347956 A1* | 12/2017 | Zegarelli | A61B 5/682 |
| 2018/0000563 A1* | 1/2018 | Shanjani | A61B 5/682 |
| 2018/0078344 A1* | 3/2018 | Falkel | A61C 7/36 |
| 2018/0085059 A1 | 3/2018 | Lee | |
| 2018/0169504 A1* | 6/2018 | Williams | A63B 71/085 |
| 2019/0099129 A1* | 4/2019 | Kopelman | A61B 5/682 |
| 2019/0175104 A1 | 6/2019 | Malik | |
| 2019/0223770 A1* | 7/2019 | Malik | A61B 5/14546 |
| 2019/0261889 A1* | 8/2019 | White | A61B 5/682 |
| 2019/0380863 A1* | 12/2019 | Mauclaire | A61F 5/566 |
| 2020/0008744 A1* | 1/2020 | Stitzel, Jr. | A61B 5/682 |
| 2020/0029821 A1* | 1/2020 | Yoshida | A61B 5/0088 |
| 2020/0037951 A1* | 2/2020 | Haggiag | A61B 5/389 |
| 2020/0038295 A1 | 2/2020 | Rouse | |
| 2020/0093571 A1 | 3/2020 | Shanjani | |
| 2020/0113654 A1* | 4/2020 | Akselrod | A61B 5/0534 |
| 2020/0147473 A1* | 5/2020 | Maloney | A63B 71/085 |
| 2020/0345534 A1* | 11/2020 | Lucas | A61B 5/682 |
| 2020/0375528 A1* | 12/2020 | Flanagan | A61B 5/087 |
| 2021/0113832 A1* | 4/2021 | Herron | A61N 1/0548 |
| 2021/0161633 A1* | 6/2021 | Makin | A61C 19/04 |
| 2021/0275345 A1* | 9/2021 | Pumphrey, Jr. | A61F 5/566 |
| 2022/0008243 A1* | 1/2022 | Osorio Martini | A61B 5/0008 |
| 2022/0117777 A1* | 4/2022 | Lasry | A61F 5/566 |
| 2022/0142746 A1* | 5/2022 | Klare | A61C 7/36 |
| 2023/0210453 A1* | 7/2023 | Brawn | A61C 19/06 |
| | | | 433/6 |

FOREIGN PATENT DOCUMENTS

| | | |
|---|---|---|
| CN | 106491220 A | 3/2017 |
| CN | 208447812 U | 2/2019 |
| CN | 111902184 A | 11/2020 |
| WO | 2000044284 A2 | 8/2000 |
| WO | 2018132435 A1 | 7/2018 |
| WO | 2022100473 A1 | 5/2022 |

OTHER PUBLICATIONS

International Search Report and Written Opinion received for PCT Application Serial No. PCT/CN2021/127949 dated Jan. 26, 2022, 11 pages.

* cited by examiner

EMBEDDED ORAL SENSOR PLATFORM

BACKGROUND

The present invention relates to dental devices. More specifically, the present invention relates to an embedded oral teeth guard device.

To prevent the damage resulting from grinding, dental professionals often prescribe a dental protector, commonly referred to as a night guard or a splint. The mouth guard acts as a protective barrier between the upper and lower sets of teeth and is typically worn at night while the patient sleeps. The guard typically covers the upper set of teeth, thus separating both sets of teeth.

Oftentimes, dentists will make a mold of a patient's mouth in order to create a custom-fitted mouth guard. Such devices generally reduce the damage that grinding can cause to teeth and supporting bone structure.

SUMMARY

According to one aspect of the present invention, an oral device is provided, comprising: a mouthpiece suitable to detachably engage teeth of an upper jaw comprising: an adhesive layer configured to attach a hermetically sealed chamber to the mouthpiece, wherein the hermitically sealed chamber fits within a concave space created by the mouthpiece, wherein the hermetically sealed chamber comprises two layers; and a pressure sensor, a microphone, an optical sensor, a temperature sensor, a communications module, a storage enclosure, and a biosensor are operably connected within the hermetically sealed chamber.

According to another aspect of the present invention an oral device is provided, comprising: a flexible substrate comprising two layers that are hermetically sealed and shaped in a rectangular manner, wherein a pressure sensor, a microphone, an optical sensor, a temperature sensor, a communications module, a storage enclosure, and a biosensor disposed within and are operably connected within the hermetically sealed chamber.

According to another aspect of the present invention an oral device is provided comprising: a mouthpiece suitable to detachably engage teeth of an upper jaw comprising: an adhesive layer configured to attach a hermetically sealed chamber to the mouthpiece, wherein the hermitically sealed chamber fits within a concave space created by the mouthpiece, wherein the hermetically sealed chamber comprises two layers; and a pressure sensor, a microphone, an optical sensor, a temperature sensor, a communications module, a storage enclosure, a bridge and amplifier circuit, an analog to digital converter, a pressure sensor, and a biosensor are operably connected within the hermetically sealed chamber, wherein the pressure sensor utilizes a piezoelectric film sensor or a strain gauge force transducer.

BRIEF DESCRIPTION OF THE DRAWINGS

Preferred embodiments of the present invention will now be described, by way of example only, with reference to the following drawings, in which.

DETAILED DESCRIPTION

Embodiments of the present invention recognize deficiencies of current mouth guards and bite measurement tools. Typically, existing mouth guards and bite measurement systems are bulky and do not conform to a user's mouth. Further, existing solutions typically lack an ability to perform electro-chemical analysis using the user's saliva while inserted in a user's mouth. Current solutions have a fixed time period or duration in which the mouth guard or measurement device is affixed to the user. Embodiments of the present invention recognize these deficiencies and provide solutions for an improve mouth guard. For example, embodiments of the present invention provide a microsystem on a flexible platform with multiple pressure sensors, electro-chemical sensors, optical sensors, a microcontroller, and communications module that can be worn for longer periods of time. Embodiments of the present invention can, while embedded or otherwise affixed to a user, determine tooth strength, tooth density, provide tissue, and nerve monitoring, and detect presence or absence of gum disease.

Figure 1:
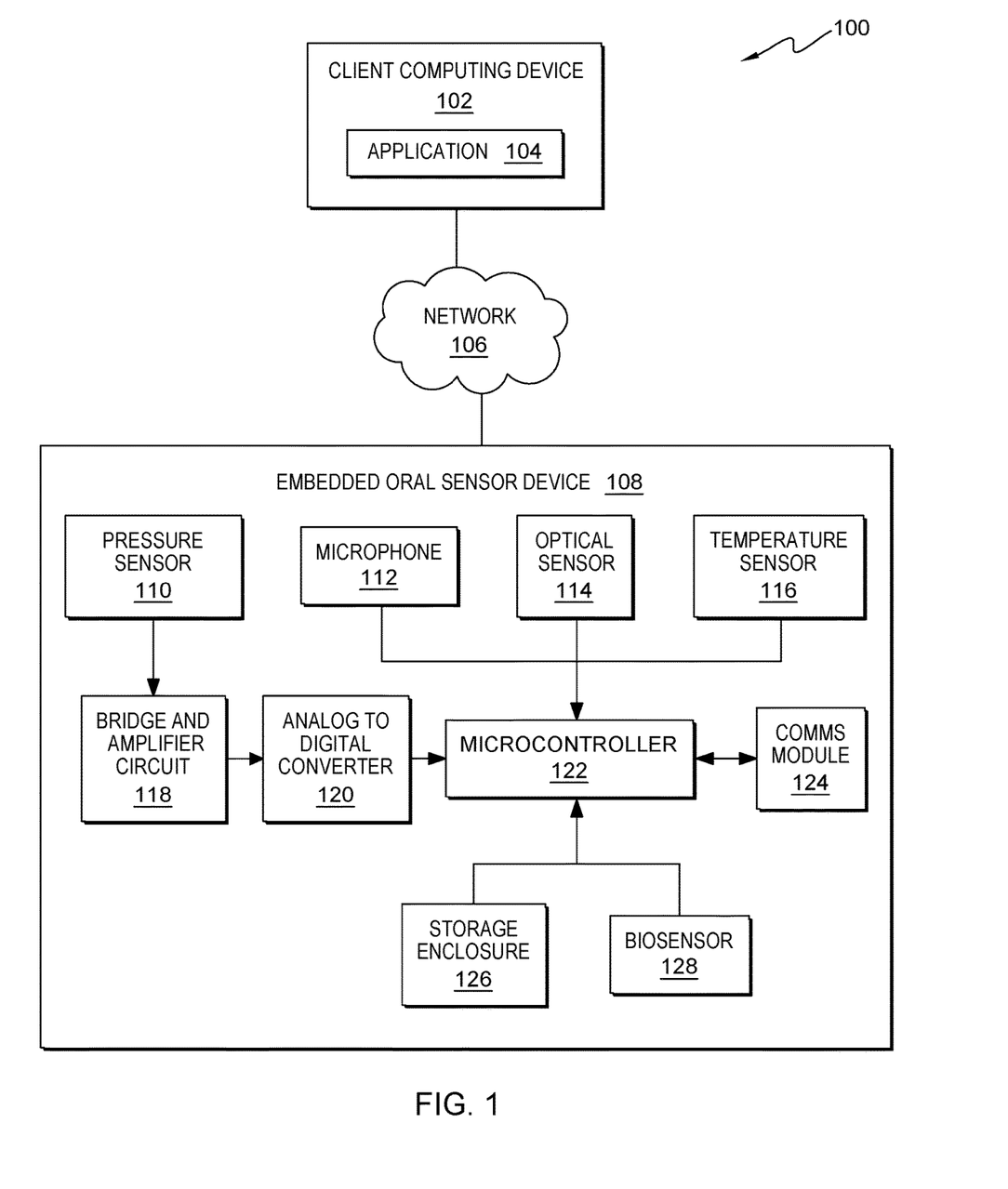
FIG. 1 depicts a block diagram of a computing environment, in accordance with an embodiment of the present invention.

FIG. 1 is a functional block diagram illustrating a computing environment, generally designated, computing environment 100, in accordance with one embodiment of the present invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Computing environment 100 includes client computing device 102 and server computer 108, all interconnected over network 106. Client computing device 102 can be a standalone computer device, a management server, a webserver, a mobile computing device, or any other electronic device or computing system capable of receiving, sending, and processing data. In other embodiments, client computing device 102 can represent a server computing system utilizing multiple computers as a server system, such as in a cloud computing environment. In another embodiment, client computing device 102 can be a laptop computer, a tablet computer, a netbook computer, a personal computer (PC), a desktop computer, a personal digital assistance (PDA), a smart phone, or any programmable electronic device capable of communicating with various components and other computing devices (not shown) within computing environment 100. In another embodiment, client computing device 102 represents a computing system utilizing clustered computers and components (e.g., database server computers, application server computers, etc.) that act as a single pool of seamless resources when accessed within computing environment 100. In some embodiments, client computing device 102 is a single device. Client computing device 102 may include internal and external hardware components capable of executing machine-readable program instructions, as depicted and described in further detail with respect to FIG. 8.

In this embodiment, client computing device 102 is a user device associated with a user and includes application 104. Application 104 communicates with embedded oral sensor device 108 (e.g., using TCP/IP) to measure and transmit biometric information. Application 104 can further communicate with embedded oral sensor device 108 to receive transmitted biometric information and subsequently analyze received biometric information as described in greater detail with regard to FIG. 6.

Network 106 can be, for example, a telecommunications network, a local area network (LAN), a wide area network (WAN), such as the Internet, or a combination of the three, and can include wired, wireless, or fiber optic connections. Network 106 can include one or more wired and/or wireless networks that are capable of receiving and transmitting data, voice, and/or video signals, including multimedia signals that include voice, data, and video information. In general, network 106 can be any combination of connections and protocols that will support communications among client computing device 102 and embedded oral sensor device 108, and other computing devices (not shown) within computing environment 100.

In this embodiment, embedded oral sensor device 108 measures and transmits biometric information. In some embodiments, embedded oral sensor device 108 can subsequently analyze the measured biometric information.

Embedded oral sensor device 108 comprises six layers that can be configured into any optimal desired shape. For example, in one embodiment, embedded oral sensor device 108 can be shaped into a mouthpiece dimensioned device (e.g., in a retainer framed shape). In another embodiment, embedded oral sensor device 108 can be shaped in a rectangular fashion, sized to fit into a user's mouth and cover the user's teeth.

In this embodiment, embedded oral sensor device 108 includes pressure sensor 110, microphone 112, optical sensor 114, temperature 116, bridge and amplifier circuit118, analog to digital converter 120, microcontroller 112, communications module124, storage enclosure 126, and biosensor 128, each of which are embedded in the second of six layers.

Pressure sensor 110 is a sensor embedded within embedded oral sensor device 108 that uses the piezoelectric effect or strain gauge to measure changes in pressure, acceleration, temperature, strain, or force by converting them to an electrical charge. In this example diagram, only one instance of pressure sensor 110 is shown, however, in this embodiment, there are two instances of pressure sensor 110. For example, one pressure sensor can be positioned on one side (e.g., a left side) and another pressure sensor can be positioned on the opposite side (e.g., a right side). In this manner, embedded oral sensor device 108 can take continuous measurements using pressure sensor 110 to measure changes in a user's bite, teeth strength, bite strength, and frequency. Pressure sensor 110 can include analog to digital (A/D) converters (e.g., analog to digital converter 120), a respective microcontroller and a register as discussed in greater detail with regard to 5B. Pressure sensor 110 communicates with bridge and amplifier circuit 118 such that they drive a single floating load (bridge) or a single common load (parallel), to increase the amount of power available in different situations. In some embodiments, pressure sensor 110 can be a piezoelectric film sensor. In some embodiments, pressure sensor 110 can also be a strain gauge force transducer.

Microphone 112 can be an integrated MEMS microphone and can provide information about bruxing and obstructive sleep apnea. Microphone 112 is also embedded and captures audio by converting sound waves into an electrical signal. This signal can be amplified as an analog signal or may be converted to a digital signal, which can be processed by a computer or other digital audio device (e.g., via analog to digital converter 120).

Optical sensor 114 can monitor the health of gum tissues, nerves, blood oxygen level, breathing patterns, gum disease identification and does so by converting light rays into electronic signals. It measures the physical quantity of light and then translates it into a form that is readable by an instrument. In some embodiments optical sensor 114 can be an electro-optical sensor that convert light, or a change in light, into an electronic signal. For example, in some embodiments optical sensor 114 can detect electromagnetic radiation from the infrared up to the ultraviolet wavelengths.

Temperature sensor 116 measures the temperature of its environment and converts the input data into electronic data to record, monitor, or signal temperature changes.

Storage enclosure 126 is a storage receptacle capable of being opened and closed at regular, fixed intervals of time. In general, storage enclosure 126 contains one or more ameliorative medicine. In some embodiments medicine can be optimized to fit within storage enclosure 126 and be dispersed in the form of pills, ointments, creams etc. to facilitate treatment.

Biosensor 128 is used for the detection of a chemical substance, that combines a biological component (e.g., tissue, organelles, cell receptors, enzymes, etc.) with a physicochemical detector (e.g., a transducer) that transforms one signal into another one and works in a physicochemical way: optical, piezoelectric, electrochemical, electrochemiluminescence etc., resulting from the interaction of with the biological element to measure and quantify. For example in some instances, biosensor 128 can help measure chemical composition (pH, impedance, etc.) through saliva.

Each of pressure sensor 110, microphone, 112, optical sensor 114, temperature sensor 116, storage enclosure 126, and biosensor 128 are connected to microcontroller 122. Microcontroller 122 is compact integrated circuit designed to govern operations of the respective sensors and modules. In this embodiment, microcontroller 122 includes a processor, memory and input/output (I/O) peripherals on a single chip (not shown). In some embodiments, microcontroller 122 can include an instance of application 104 to subsequently analyze received biometric information.

Communications module 124 is used for exchanging data between fixed and mobile devices over short distances using scientific and medical radio bands, from 2.402 GHz to 2.480 GHz. For example, communications module 124 can be used by embedded oral sensor device 108 to transmit collected information from each of the one or more sensors (e.g., pressure sensor, optical sensor, temperature sensor, biosensor, etc.) to client computing device 102 via network 106.

Figure 2A:
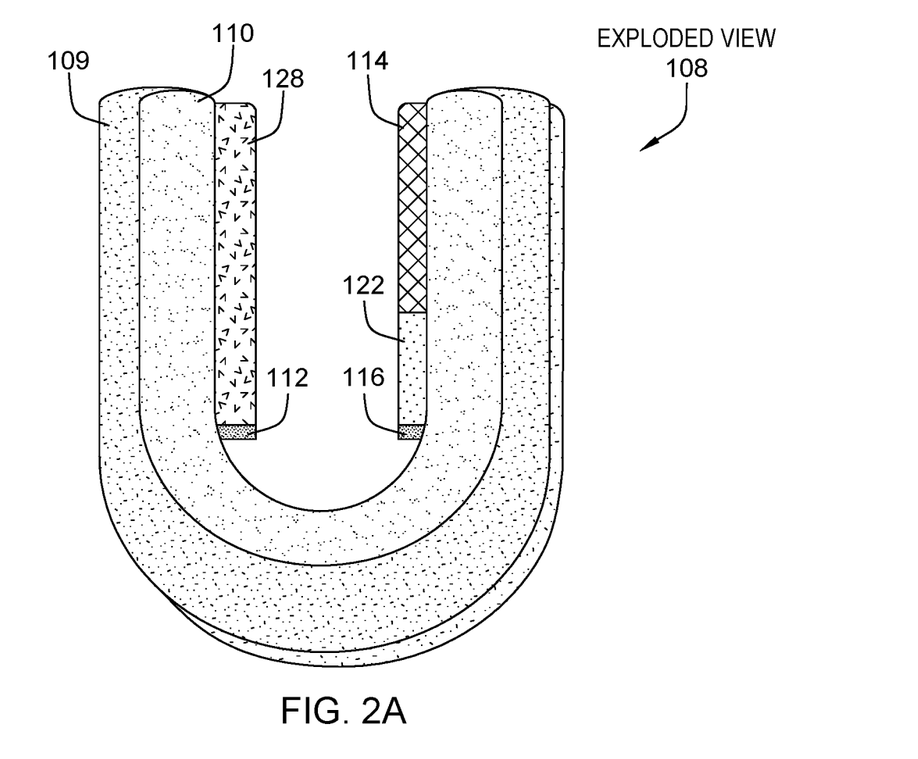
FIG. 2A is an exploded view of an embedded oral sensor device, in accordance with an embodiment of the present invention.

FIG. 2A is an exploded view of an embedded oral sensor device, in accordance with an embodiment of the present invention.

In this embodiment, embedded oral sensor device 108 includes base layer 109 molded into a shape of a mouth piece (e.g., in the shape of a horseshoe) that functions as a cover or guard that is suitable to detachably engage teeth and a pallet of an upper jaw. In this embodiment, base layer 109 is made of plastic and is custom molded to the wearer's mouth at each individual tooth.

Positioned inside and affixed to base layer 109 is an adhesive layer (not shown) located in the concave space created by the horseshoe shape of base layer 109. The adhesive layer adheres a first film layer (not shown) to the base layer. Disposed within the first film layer is pressure sensor 110, biosensor 128, optical sensor 114, temperature sensor 116, communications module 124 (shown as comms module 124), and microcontroller 122 all interconnected with appropriate wiring. A second film layer hermetically seals each of pressure sensor 110, biosensor 128, optical sensor 114, temperature sensor 116, communications module 124, and microcontroller 122, that is the first and second film layers create a hermetic seal.

In this embodiment, pressure sensor 110 is positioned within the first layer and second layer such that pressure sensor 110, when worn, is situated or otherwise lies flush with a biting surface of one or more teeth. For example, in this embodiment, where base layer 109 is a horseshoe shape, pressure sensor 110 can have a plurality of instances each of which interfaces or lies flush with multiple teeth of the wearer's upper or lower jaw. In some embodiments pressure sensor 110 lies flush with only a molar tooth).

Biosensor 128 is positioned within the first layer and second layer such that when embedded oral sensor device 108 is worn, biosensor 128 is situated adjacent to another biting surface of one or more teeth (e.g., adjacent to the molar tooth). Microphone 112 is positioned to be adjacent to biosensor 128 such that when worn, interfaces with a biting surface of a tooth adjacent to the biting surface that interfaces with biosensor 128

Optical sensor 114 is placed opposite of pressure sensor 110, that is, on an opposite side of pressure sensor 110 such that optical sensor 114 lies flush with a biting surface of one or more teeth opposite of the tooth pressure sensor 110 (e.g., the opposite side molar tooth). In this embodiment, microcontroller 122 and Communications 124 are situated adject to each other, and when embedded oral sensor device 108 is worn, positions microcontroller 122 and Communications 124 flush with a biting surface of one or more teeth adjacent to a respective one or more teeth that interfaces with optical sensor 114. Situated next to microcontroller 122 and Communications 124, is temperature sensor 116.

When the wearer begins to grind (e.g., brux) or bite, pressure sensor 110 is engaged, microcontroller 122 transmits a signal to activate one or more additional sensors (e.g., pressure sensor 110, biosensor 128, optical sensor 114, and temperature sensor 116, etc.) to collect additional information.

Microcontroller 122 can then balance and amply analog signals from each respective module using bridge and amplifier circuit 118 (not shown) and analog to digital converter 120 (not shown). Microcontroller 122 can then transmit instructions to communications module 124 to transmit the collected information for further analysis. In some embodiments, microcontroller 122 can subsequently transmit an instruction (via communications module 124) to send a wake-up signal to one or more other connected device (e.g., an alarm clock) to wake up the user to prevent the user from grinding his or her teeth. In yet other embodiments, microcontroller 122 can analyze received biometric information.

Figure 2B:
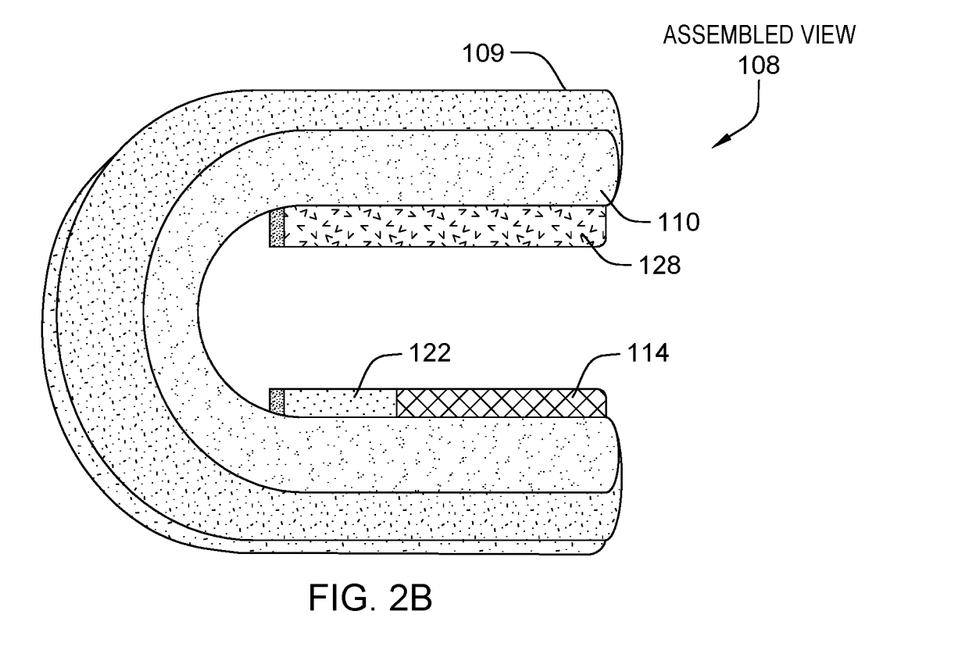
FIG. 2B is an assembled view of an embedded oral sensor device, in accordance with an embodiment of the present invention.

FIG. 2B is an assembled view of an embedded oral sensor device, in accordance with an embodiment of the present invention. For illustrative purposes, some elements of embedded oral sensor device 108 are not shown. For example, as shown, microphone 114 and temperature sensor 116 are obscured from view.

In another embodiment where the assembled, embedded oral sensor device (embedded oral sensor device 108) takes on the form of a denture, embedded oral sensor device can use a number of adhesive compositions to affix the mouth piece (e.g., a denture in the shape of a horseshoe) to attach to teeth surfaces and a pallet of the upper jaw for longer periods of time. For example, in some embodiments, methyl vinyl ether-maleic anhydride copolymer can be used. In other embodiments, karaya gum, tragacanth, acacia, pectin, gelatin, carboxymethylcellulose, mineral oil, antimicrobial agents (e.g., ethanol, sodium borate, sodium tetraborate, hexchlorophone, etc.) non-toxic additives, and flavoring agents (e.g., peppermint oil, wintergreen oil) may be used.

Figure 3:
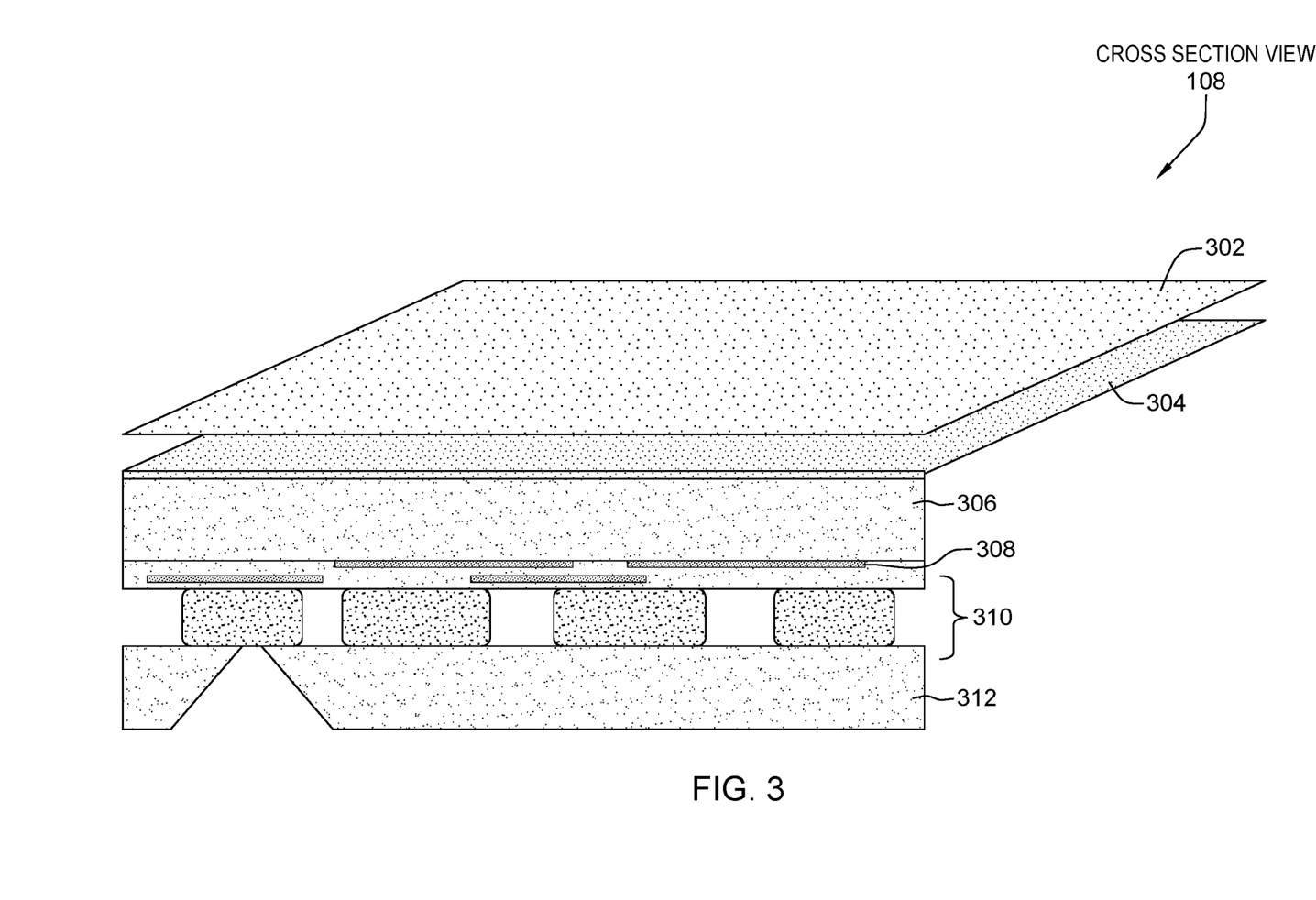
FIG. 3 is a cross section view of an embedded oral sensor device, in accordance with an embodiment of the present invention.

FIG. 3 is a cross section view of an embedded oral sensor device, in accordance with an embodiment of the present invention.

In this example, embedded oral sensor device 108 depicts layer 302 which is representative of the base layer (e.g., base layer 109) discussed in FIG. 2A. Layer 302 is molded into a shape of a mouth piece (e.g., in the shape of a horseshoe) that functions as a cover or guard that is suitable to detachably engage teeth and a pallet of an upper jaw. In this embodiment, base layer 109 is made of plastic and is custom molded to the wearer's mouth at each individual tooth.

Positioned inside and affixed to layer 302 is adhesive layer 304 located in the concave space created by the horseshoe shape of layer 302. The adhesive layer adheres a first film layer (e.g., film layer 306) to the base layer (e.g., layer 302). Disposed within first film layer (e.g., film layer 306) are one or more sensors 310. Sensors 310 include pressure sensor 110, biosensor 128, optical sensor 114, temperature sensor 116, communications module 124, and microcontroller 122 all interconnected with wiring 308. A second film layer (e.g., film layer 312) hermetically seals each of pressure sensor 110, biosensor 128, optical sensor 114, temperature sensor 116, communications module 124, and microcontroller 122, that is the first and second film layers create a hermetic seal that is impervious to water or saliva.

Figure 4A:
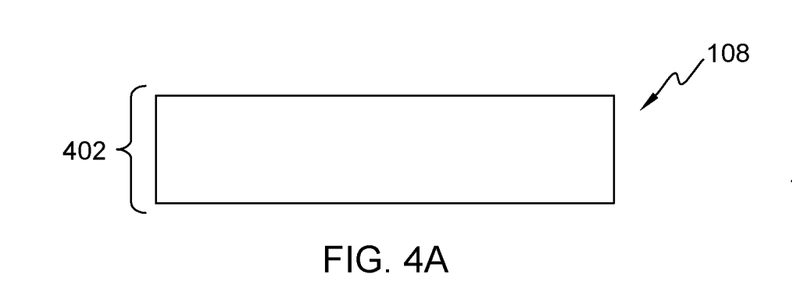
FIGS. 4A-C show alternate perspective views of an embedded oral sensor device, in accordance with an embodiment of the present invention.
Figure 4B:
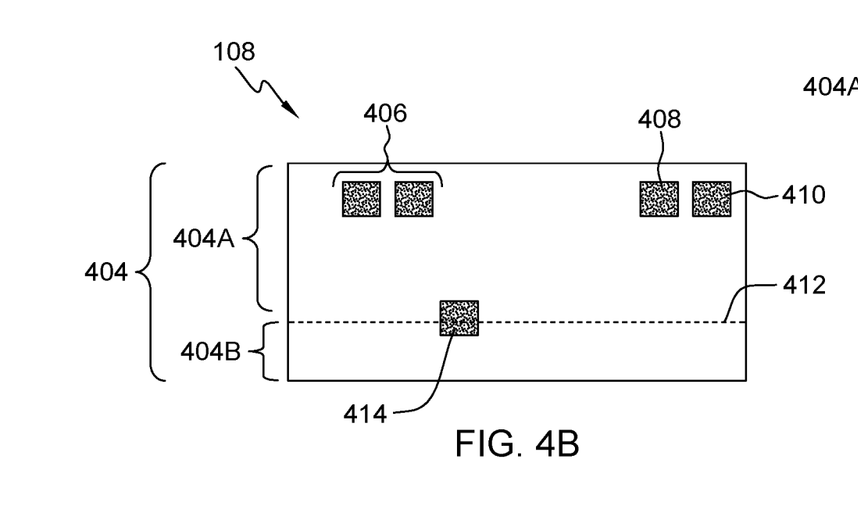
Figure 4C:
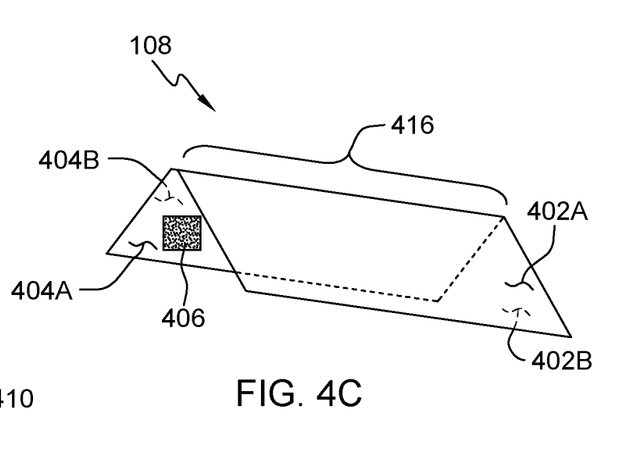

FIGS. 4A-C show alternate perspective views of an embedded oral sensor device, in accordance with an embodiment of the present invention.

FIGS. 4A and 4B describe an alternate embodiment of the present invention that show different sides or surfaces of a film.

For example, in some embodiments, embedded oral sensor 108 can be a flexible substrate, shaped in a rectangular fashion. This flexible substrate can be a hermetically sealed chamber created by the first and second film layer containing one or more sensors shaped in a rectangular manner. Optionally, a guard layer can be affixed to the hermetically sealed chamber via an adhesive In FIG. 4A, the first and second film layer when combined form two sides or surfaces. In this embodiment, side 402 corresponds to a front surface while side 404 denotes an opposite side or back surface.

FIG. 4B describes the opposite side of the sealed chamber. In this example, side 404 comprise two portions: upper portion 404A and lower portion 404B. In this embodiment, upper portion 404 makes up three quarters of the length of side 404 while lower portion 404 makes up the remaining one quarter of the length of side 404. The portions are split along axis 412.

Embedded on upper portion 404A are sensors 406, 408, and 410. In some embodiments, sensors 406, 408, and 410 can be integrated to lie on top of the film layer to directly interact or lie flush with one or more teeth, when embedded oral sensor device 108. In general, sensors 406, 408, and 410 are representative of one or more modules that can be embedded within the first and second film layers. For example, sensors 406, 408 and 410 can be an optical sensor, pressure gauge, a microcontroller bundle including a communications module, and a battery. Embedded between upper portion 404A and lower portion 404B is storage enclosure 414 (e.g., functionally similar to storage enclosure 126).

FIG. 4C shows an embedded oral sensor device made of film, folded over. In this example, only one sensor is shown for illustrative purposes. In this example, sides 402 and 404 are created when the sealed film layer is folded over line 416. When folded over sides 402 and 404 each have additional surfaces. For example, side 402 can have a front side (e.g., portion 402A, first surface) that interfaces with the superior lip of the wearer's mouth and functions as a guard or barrier to protect embedded oral sensor device 108 in the cavity of the wearer's mouth. The back side or posterior portion of side 402 (e.g., portion 402B, second surface) interfaces with the anterior (front side/portion) portion of the tooth (e.g., anterior portion of the central incisor). In some embodiments, portion 402B can be embedded with a storage enclosure (e.g., storage enclosure 126).

Embedded oral device 108 can then be applied such that the anterior portion of the back side (e.g., portion 404A, third surface) interfaces with the posterior portion of a respective tooth (e.g., the posterior portion of the central incisor). The posterior portion of the back side (e.g., portion 404B, fourth surface) functions as a guard or barrier to protect embedded oral device 108 from the cavity of the wearer's mouth.

Figure 5A:
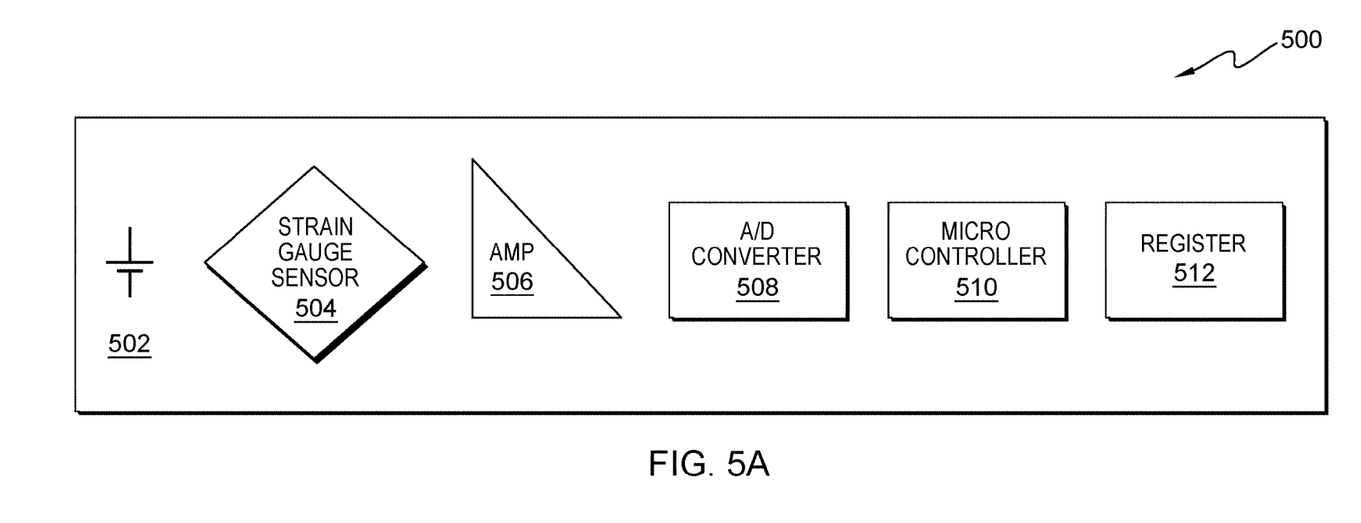
FIGS. 5A and 5B show types of pressure sensors based on strain gauge and piezoelectric sensor units, in accordance with an embodiment of the present invention.
Figure 5B:
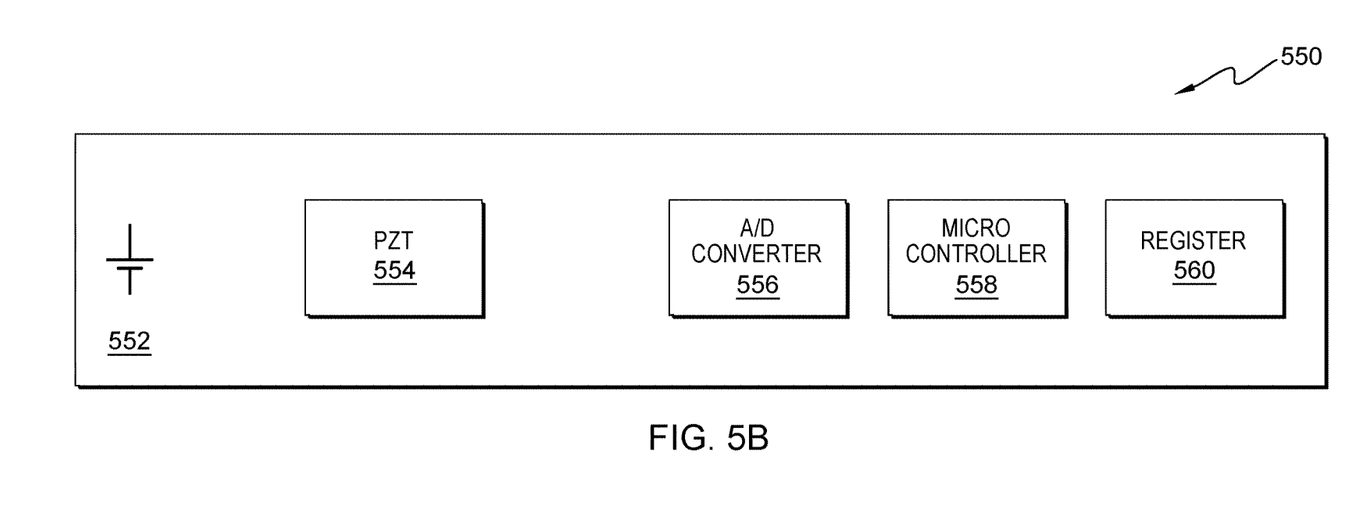

FIGS. 5A and 5B show types of pressure sensors based on strain gauge and piezoelectric sensor units, in accordance with an embodiment of the present invention.

FIG. 5A shows a block diagram of a stain gauge sensor unit. In this example, pressure sensor unit 500 functions similar to pressure sensor 110. Pressure sensor unit 500 includes battery 502, strain gauge sensor 504, amplifier circuit 506, analog to digital converter 508, microcontroller 510 and register 512. In this embodiment, pressure sensor unit 500 utilizes a Wheatstone bridge circuit to connect components 502-512. In this embodiment, strain gauge sensor 504 is based on conductive polymer and pressure sensitive ink.

FIG. 5B shows a block diagram of a piezoelectric sensor unit. In this example, pressure sensor unit 550 functions similar to pressure sensor 110. Pressure sensor unit 550 includes battery 552, piezoelectric sensor 554, analog to digital converter 556, microcontroller 558 and register 560. In this embodiment, pressure sensor unit 550 utilizes piezoelectric sensors that consists of two crystal disks with an electrode foil mounted in between. When pressure is applied, an electrical charge that can be measured using a charge amplifier. The charge is proportional to the applied pressure.

Figure 6:
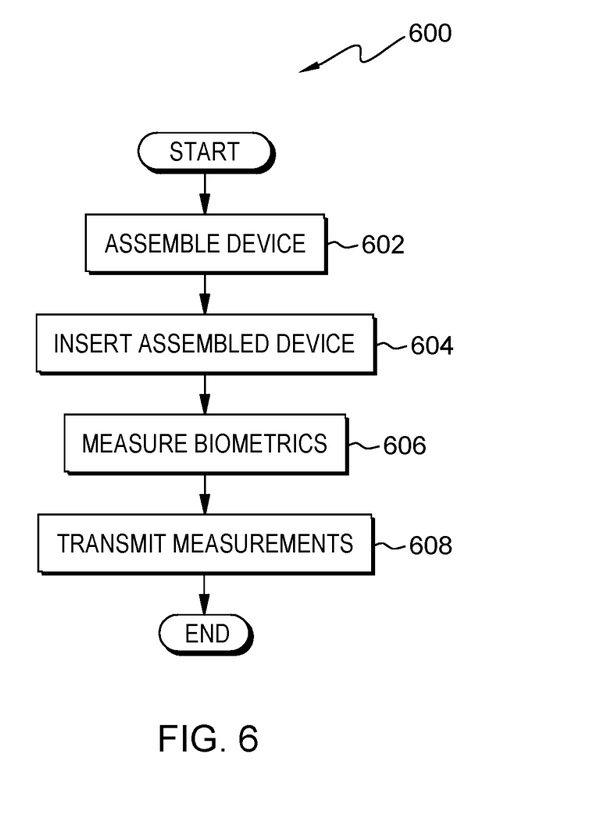
FIG. 6 is a flowchart depicting operational steps for measuring biometrics, in accordance with an embodiment of the present invention.

FIG. 6 is a flowchart 600 depicting operational steps for measuring biometrics, in accordance with an embodiment of the present invention.

In step 602, embedded oral sensor device 108 is assembled. In this embodiment, embedded oral sensor device 108 is assembled in a manner as described in FIG. 2A by creating a hermitically sealed film chamber that is then placed in the concave space created by the horseshoe shape mouthpiece (e.g., in the shape of a horseshoe) to fit within a user specific mold of the wearer's mouth.

As mentioned before, the hermetically sealed film chamber comprises two film layers that encapsulate pressure sensor 110, biosensor 128, optical sensor 114, temperature sensor 116, communications module 124, and microcontroller 122 all interconnected with appropriate wiring. The hermetically sealed film chamber can then be affixed to the concave space created by the horseshoe shape mouthpiece using any adhesive material generally available.

In step 604, the assembled embedded oral sensor device 108 is inserted into the wearers mouth affixing the assembled, embedded oral sensor device 108 to the wearer's upper jaw. In other embodiments, embedded oral sensor device 108 can be shaped and configured to fit over the wearer's lower jaw.

In step 606, embedded oral sensor device 108 measures biometrics of the wear. In this embodiment embedded oral sensor device 108 utilizes microcontroller 122 to activate and collect biometric information of the wearer. In some instances, pressure sensor 110 can be triggered when a certain threshold amount or level of pressure is exerted by the wearer (e.g., when the wearer begins to brux). In response to the threshold level of pressure exerted being met or exceeded, microcontroller 122 can then enable or otherwise trigger other modules embedded within embedded oral sensor device 108. For example, microcontroller 122 can activate microphone 112 to record audio generated by the grinding of teeth), optical sensor 114 to record what is happening, and temperature sensor 116 to record a temperature of the wearer at the time bruxing occurred. Microcontroller 122 can, in some embodiments also activate biosensor 128 to detect presence or absence of certain chemicals. When needed, microcontroller 122 can also activate the opening and closing of storage enclosure 126 to release stored biological agents (e.g., medicine or ameliorative agents) as part of a prescribed treatment plan.

In step 608, transmits measured biometrics of the wearer. In this embodiment, embedded oral sensor device 108 transmits the measured and collected biometrics to application 104 of client computing device 102 utilizing communications module 124 (via network 106). Application 104 can then subsequently analyze the collected biometric information to determine a condition (e.g., an ailment) and recommend a treatment plan. In some embodiments, application 104 may communicate with another computing device associated with the user (e.g., an alarm) to activate and wake the user.

In yet other embodiments, microcontroller 122 may contain an instance of application 104 and can perform limited analysis of the collected biometric information. In this embodiment, microcontroller 122 may process and analyze the collected information utilizing one or more machine learning and artificial intelligence algorithms.

Figure 7A:
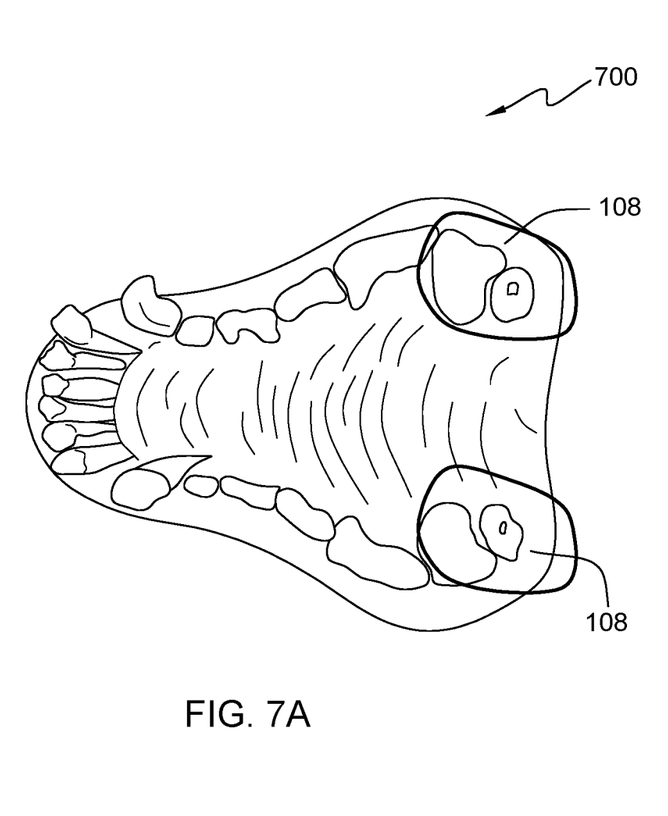
FIGS. 7A and 7B depict alternate placements of an embedded oral sensor device, in accordance with an embodiment of the present invention.
Figure 7B:
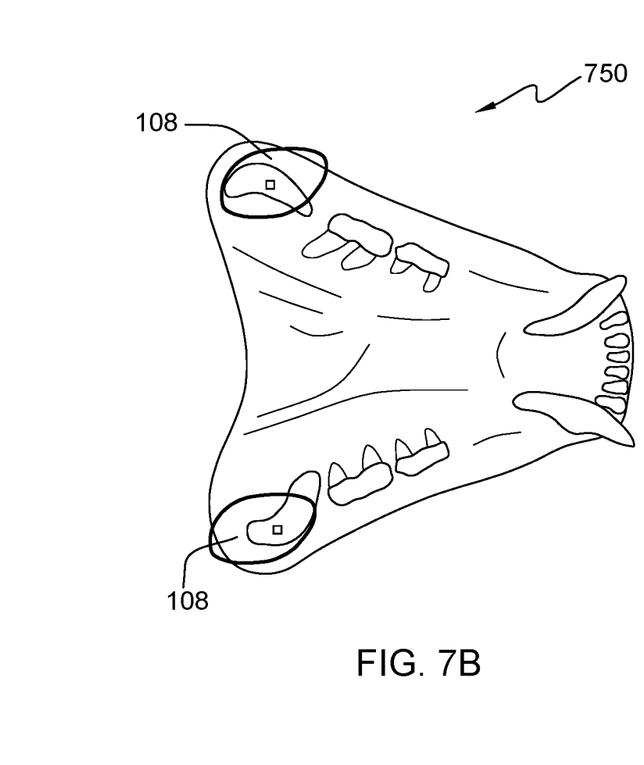

FIGS. 7A and 7B depict alternate placements of an embedded oral sensor device, in accordance with an embodiment of the present invention.

FIG. 7A depicts an alternate use case and placement of an embedded oral sensor device. In this example, example 700, embedded oral sensor device 108 can be made to spherically attach to the upper jaw molars of a canine.

FIG. 7B depicts an alternate use case and placement of an embedded oral sensor device. In this example, example 750, embedded oral sensor device 108 can be made to spherically attach to the lower jaw molars of a feline.

Figure 8:
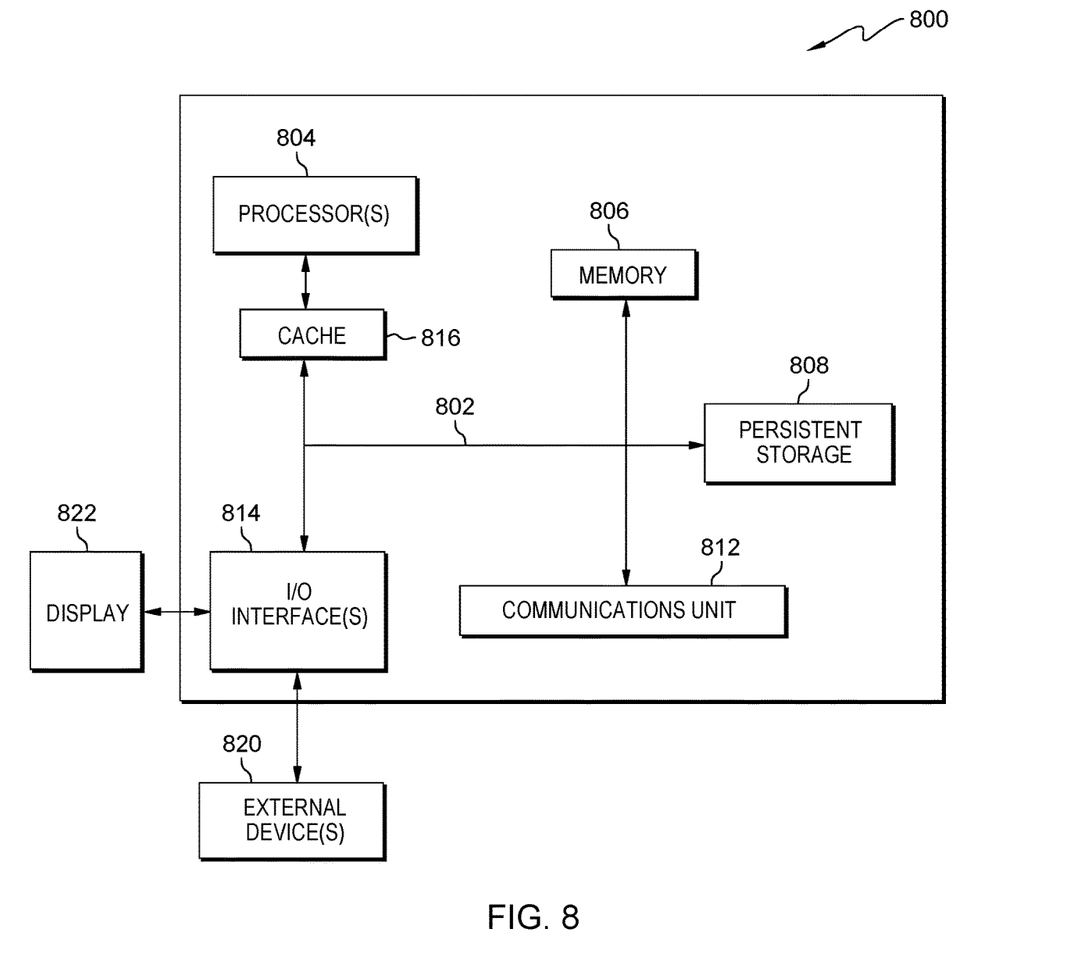
FIG. 8 is a block diagram of an example system, in accordance with an embodiment of the present invention.

FIG. 8 depicts a block diagram of components of computing systems within computing environment 100 of FIG. 1, in accordance with an embodiment of the present invention. It should be appreciated that FIG. 8 provides only an illustration of one implementation and does not imply any limitations with regard to the environments in which different embodiments can be implemented. Many modifications to the depicted environment can be made.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Computer system 800 includes communications fabric 802, which provides communications between cache 816, memory 806, persistent storage 808, communications unit 812, and input/output (I/O) interface(s) 814. Communications fabric 802 can be implemented with any architecture designed for passing data and/or control information between processors (such as microprocessors, communications and network processors, etc.), system memory, peripheral devices, and any other hardware components within a system. For example, communications fabric 402 can be implemented with one or more buses or a crossbar switch.

Memory 806 and persistent storage 808 are computer readable storage media. In this embodiment, memory 806 includes random access memory (RAM). In general, memory 806 can include any suitable volatile or non-volatile computer readable storage media. Cache 816 is a fast memory that enhances the performance of computer processor(s) 804 by holding recently accessed data, and data near accessed data, from memory 806.

Application 104 (not shown) may be stored in persistent storage 808 and in memory 806 for execution by one or more of the respective computer processors 404 via cache 816. In an embodiment, persistent storage 808 includes a magnetic hard disk drive. Alternatively, or in addition to a magnetic hard disk drive, persistent storage 808 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 808 may also be removable. For example, a removable hard drive may be used for persistent storage 808. Other examples include optical and magnetic disks, thumb drives, and smart cards that are inserted into a drive for transfer onto another computer readable storage medium that is also part of persistent storage 808.

Communications unit 812, in these examples, provides for communications with other data processing systems or devices. In these examples, communications unit 812 includes one or more network interface cards. Communications unit 812 may provide communications through the use of either or both physical and wireless communications links. Application 104 may be downloaded to persistent storage 808 through communications unit 812.

I/O interface(s) 814 allows for input and output of data with other devices that may be connected to client computing device and/or server computer. For example, I/O interface 814 may provide a connection to external devices 820 such as a keyboard, keypad, a touch screen, and/or some other suitable input device. External devices 820 can also include portable computer readable storage media such as, for example, thumb drives, portable optical or magnetic disks, and memory cards. Software and data used to practice embodiments of the present invention can be stored on such portable computer readable storage media and can be loaded onto persistent storage 808 via I/O interface(s) 814. I/O interface(s) 814 also connect to a display 822.

Display 822 provides a mechanism to display data to a user and may be, for example, a computer monitor.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. An oral device comprising:
    a flexible substrate comprising two layers that are hermetically sealed forming a hermetically sealed chamber shaped in a rectangular manner,
    wherein the two layers form two sides of the hermetically sealed chamber, and the two sides include:
    a first side having a first surface; and
    a second side having a second surface opposite the first surface, wherein the second surface is substantially a same length as the first surface and wherein the second surface has an upper portion defined by a first width that is approximately three quarters of the width of the second surface and a lower portion defined by a second width that is approximately one quarter of the width of the second surface, wherein the upper portion and the lower portion are adjoined with a split line along a horizontal axis of the second surface, and wherein the first width and the second width comprise an entirety of the width of the second surface,
    wherein an optical sensor, a pressure gauge, and a microcontroller bundle are disposed in, and are operatively connected to the upper portion of the second surface, and wherein a storage enclosure is disposed in the lower portion of the second surface and opens and closes at fixed intervals of time; and
    a guard layer affixed to the hermetically sealed chamber.

2. The oral device of claim 1, wherein the flexible substrate, upon being folded in half includes four surfaces, the four surfaces including the first surface and the second surface.

3. The oral device of claim 2, wherein the four surfaces comprise:
    the first surface, wherein the first surface, upon insertion into a wearer's mouth, interfaces with a superior lip of the wearer and functions as a barrier between the oral device and an oral cavity of the wearer;
    the second surface, wherein the second surface, upon insertion into the wearer's mouth, interfaces with a respective anterior portion of one or more teeth;
    a third surface, wherein the third surface, upon insertion into the wearer's mouth, interfaces with a respective posterior portion of the one or more teeth; and
    a fourth surface, wherein the fourth surface, upon insertion into the wearer's mouth, functions as another barrier between the oral device and the oral cavity of the wearer.

4. The oral device of claim 3, wherein the storage enclosure is embedded within the second surface.

5. The oral device of claim 3, wherein a pressure sensor, a microphone, the optical sensor, a temperature sensor, a communications module, and a biosensor are disposed on the third surface.

6. The oral device of claim 5, wherein the pressure sensor is a strain gauge film sensor.

7. The oral device of claim 6, wherein the pressure sensor utilizes a piezoelectric film sensor.

8. The oral device of claim 1, further comprising:
an adhesive layer that affixes the flexible substrate comprising the two layers that are hermetically sealed to a denture device.

9. The oral device of claim 8, wherein the adhesive layer is selected from a group consisting ofmethyl vinyl ether-maleic anhydride copolymer, karaya gum, tragacanth, acacia, pectin, gelatin, carboxymethylcellulose, and mineral oil.

10. The oral device of claim 9, further comprising: antimicrobial agents non-toxic additives, and flavoring agents.

11. An oral device comprising:
a flexible substrate comprising two layers that are hermetically sealed forming a hermetically sealed chamber, wherein the two layers form two sides of the hermetically sealed chamber, and the two sides include:

a first side having a first surface; and a second side having a second surface opposite the first surface, wherein the second surface has:

an upper portion defined by a first width of a total width of the second surface; and a lower portion defined by a second width that is a second width of the total width of the second surface, wherein the upper portion and the lower portion are adjoined with a split line along a horizontal axis of the second surface, and wherein the upper portion and the lower portion comprise an entirety of the width of the second surface, wherein an optical sensor, a pressure gauge, and a microcontroller bundle are disposed in, and are operatively connected to the upper portion of the second surface, and wherein a storage enclosure is disposed in the lower portion of the second surface and opens and closes.

* * * * *